United States Patent [19]

Malis et al.

[11] Patent Number: 5,465,712
[45] Date of Patent: Nov. 14, 1995

[54] RESUSCITATION MASK HAVING RIBS IN THE AIR FLOW CONDUIT AND MASK BODY

[75] Inventors: Jerry Malis, King of Prussia, Pa.;
Jonathan J. Rosen, Alpharetta, Ga.;
Martin T. Mortimer, Telford, Pa.;
Alfred V. Vasconcellos, Cranston, R.I.

[73] Assignee: Valley Forge Scientific Corporation, Oaks, Pa.

[21] Appl. No.: 100,592

[22] Filed: Jul. 30, 1993

[51] Int. Cl.⁶ .......................... A62B 18/02; A62B 18/10
[52] U.S. Cl. .................. 128/205.25; 128/207.12; 128/912; 128/203.11
[58] Field of Search .............. 128/202.28, 202.29, 128/203.11, 203.25, 205.11, 205.13, 205.25, 206.21, 206.24, 206.26, 206.27, 206.28, 207.11, 207.12, 912

[56] References Cited

U.S. PATENT DOCUMENTS

| | | | |
|---|---|---|---|
| 3,042,035 | 7/1962 | Coanda . | |
| 3,252,457 | 5/1966 | Monaco et al. . | |
| 3,286,710 | 11/1966 | Bartlett . | |
| 3,802,428 | 4/1974 | Sherman . | |
| 3,982,532 | 9/1976 | Halldin et al. . | |
| 4,196,725 | 4/1980 | Gunderson | 128/205.25 |
| 4,231,363 | 11/1980 | Grimes | 128/205.25 |
| 4,233,972 | 11/1980 | Hauff et al. | 128/205.12 |
| 4,263,908 | 4/1981 | Mizeral | 128/205.25 |
| 4,266,540 | 5/1981 | Panzik et al. | 128/207.13 |
| 4,297,999 | 11/1981 | Kitrell | 128/205.16 |
| 4,446,864 | 5/1984 | Watson et al. | 128/207.14 |
| 4,449,525 | 5/1984 | White et al. | 128/203.11 |
| 4,459,983 | 7/1984 | Beyreuther et al. | 128/205.24 |
| 4,469,097 | 9/1984 | Kelman | 128/205.22 |
| 4,494,538 | 1/1985 | Ansite | 128/205.25 |
| 4,497,318 | 2/1985 | Donmichael | 128/202.28 |
| 4,520,811 | 6/1985 | White et al. | 128/203.11 |
| 4,559,940 | 12/1985 | McGinnis | 128/206.26 |
| 4,579,114 | 4/1986 | Gray et al. | 128/203.11 |
| 4,622,964 | 11/1986 | Flynn | 128/205.24 |
| 4,655,213 | 4/1987 | Rapoport et al. | 128/205.25 |
| 4,697,587 | 10/1987 | Marinkovich | 128/203.11 |
| 4,811,730 | 3/1989 | Milano | 128/203.11 |
| 4,819,628 | 4/1989 | Eisenberg et al. | 128/203.11 |
| 4,834,085 | 5/1989 | Webster, II | 128/203.11 |
| 4,858,605 | 8/1989 | Levy | 128/203.11 |
| 4,886,057 | 12/1989 | Nave | 128/203.11 |
| 4,907,584 | 3/1990 | McGinnis | 128/206.24 |
| 4,909,245 | 3/1990 | Wollenhaupt | 128/203.11 |
| 4,942,873 | 7/1990 | Irwin et al. | 128/203.11 |
| 4,944,291 | 7/1990 | Robertson, II et al. | 128/203.11 |
| 5,005,571 | 4/1991 | Dietz | 128/205.25 |
| 5,022,392 | 6/1991 | Yeakel | 128/202.28 |
| 5,048,516 | 9/1991 | Söderberg | 128/205.25 |
| 5,065,756 | 11/1991 | Rapoport | 128/204.18 |
| 5,074,297 | 12/1991 | Venegas | 128/204.18 |

(List continued on next page.)

FOREIGN PATENT DOCUMENTS

| 1226504 | 9/1987 | Canada | 128/202.28 |
|---|---|---|---|

*Primary Examiner*—Kimberly L. Asher
*Attorney, Agent, or Firm*—Panitch Schwarze Jacobs & Nadel

[57] ABSTRACT

Briefly stated, the present invention comprises a resuscitation mask for administering artificial respiration to a patient. The respiration mask has a container for defining an interior region between the container and the face of the patient. Two conduits are provided through the container wall in order to define two air flow passageways which are in fluid communication with the internal region. A valve is disposed in one air flow passageway for permitting air flow into the internal region and preventing air flow from the internal region. A vent is provided to reduce pressure within the internal region in response to an increase in pressure within the internal region. The container is generally cup-shaped and, in the preferred embodiment, it is formed with a cylindrical member coupled to the one-way air flow conduit. The other airflow passageway is adapted to be detachably coupled to an oxygen source. A pressure openable closure permits pressure within the interior region of the resuscitation mask to be released by a further conduit.

10 Claims, 4 Drawing Sheets

U.S. PATENT DOCUMENTS

| | | | |
|---|---|---|---|
| 5,088,485 | 2/1992 | Schock | 128/202.28 |
| 5,109,839 | 5/1992 | Blasdell et al. | 128/203.12 |
| 5,119,809 | 6/1992 | Gerson | 128/202.28 |
| 5,121,745 | 6/1992 | Israel | 128/202.28 |
| 5,127,397 | 7/1992 | Kohnke | 128/202.28 |
| 5,146,914 | 9/1992 | Sturrock | 128/203.11 |
| 5,165,396 | 11/1992 | Don Michael et al. | 128/203.11 |

RESUSCITATION MASK HAVING RIBS IN THE AIR FLOW CONDUIT AND MASK BODY

BACKGROUND OF THE INVENTION

The present invention relates to resuscitation devices and, more particularly, to a mask for cardiopulmonary resuscitation.

As used herein, mouth-to-mouth resuscitation refers to methods in which air is forced at regular intervals from the lungs of a rescuer into the lungs of a patient who has stopped breathing in order to provide the interchange of air necessary for respiration. If the heart of the patient has also stopped, simultaneous cardiac resuscitation is also necessary. These simultaneous resuscitation efforts are referred to as cardiopulmonary resuscitation.

Because the lips and associated facial muscles of a patient requiring mouth-to-mouth resuscitation are flaccid, it is difficult to produce a satisfactory seal with the lips of a patient using many resuscitation devices. The seal which is achieved in mouth-to-mouth resuscitation is satisfactory due to the ability of rescuers to close their lips over the mouth area of the patient and thereby conform to that area. Thus, this classic mouth-to-mouth resuscitation technique requires direct contact between the rescuer and the patient. Many potential rescuers find this aspect of the technique objectionable.

Therefore, prior art methods have been developed for performing resuscitation in which no mouth-to-mouth contact is required between the rescuer and the patient. These prior art methods may involve the insertion of a tube device into the airway of the patient. These devices included intubation devices and esophageal obturator airways. However, an effective seal must still be established over the mouth of the patient while air is forced into the patient as previously described. Many of these devices did not effectively form such a seal.

It is also known to provide cardiopulmonary resuscitation devices which include a resuscitation face mask. The face masks of the prior art were often formed of a thin flexible film which was positioned over the mouth and nose regions of the patient. It was known to position a one-way valve in a centrally located opening in these prior art film masks to permit the rescuer to blow air into the respiratory passages of the patient while preventing exhaled air from the patient from flowing into the mouth of the user.

However, when these prior art resuscitation masks were used to perform cardiopulmonary resuscitation it was necessary to alternately remove and replace the mask if the rescuer switched between forcing air into the lungs of the user and providing oxygen from an oxygen source to the patient. Additionally, if the rescuer alternated between allowing the patient to breathe unassisted and providing oxygen, the coupling of the oxygen supply had to be removed or the oxygen turned off. Removal of the mask was sometimes required in order to allow the patient to breathe unassisted thereby making periodic assistance with oxygen more difficult.

Additionally, many prior art resuscitation masks were rigid or semi-rigid making it difficult to store them in small packages. Resuscitation masks that were flexible enough to be folded into a small package for convenient storage and transportation lacked the structural integrity sometimes necessary for use in emergency situations involving cardiopulmonary resuscitation.

The resuscitation mask of the present invention is adapted to fit over the mouth and nose of a patient to provide a good seal with the face of the patient. The mask includes a tightenable head strap for securing the mask to the head of the patient, an oxygen supply port of the tapered type, and a second, larger, sealable port. The larger port is adapted to be opened to permit the patient to breathe normally once resuscitation has been accomplished while still permitting a flow of oxygen through the oxygen port as well as for patient monitoring. A generally cylindrical mouth member extends outwardly from the front of the mask and is adapted to be engaged by the mouth of a rescuer. The mouth member includes interior spacer ribs to prevent collapse of the air flow passageway through the mouth member thereby allowing air to pass therethrough when it is tightly gripped. Above the mouth member on the front face of the mask is a slot which receives a one-way duckbill valve assembly. The valve assembly permits air to flow to the patient and blocks air in the opposite direction. The slot cooperates with the valve assembly to provide a vent to permit fluid from the patient to escape from the mask.

SUMMARY OF THE INVENTION

Briefly stated, the present invention comprises a resuscitation mask for administering artificial respiration to a patient. The respiration mask has a container for defining an interior region between the container and the face of the patient. Two conduits are provided through the container wall in order to define two air flow passageways which are in fluid communication with the internal region. A valve is disposed in one air flow passageway for permitting air flow into the internal region and preventing air flow from the internal region. A vent is provided to reduce pressure within the internal region in response to an increase in pressure within the internal region. The container is generally cup-shaped and, in the preferred embodiment, it is formed with a cylindrical member coupled to the one-way air flow conduit. The other airflow passageway is adapted to be detachably coupled to an oxygen source. A pressure openable closure permits pressure within the interior region of the resuscitation mask to be released by a further conduit.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings.

DETAILED DESCRIPTION OF PREFERRED EMBODIMENTS

Figure 1:
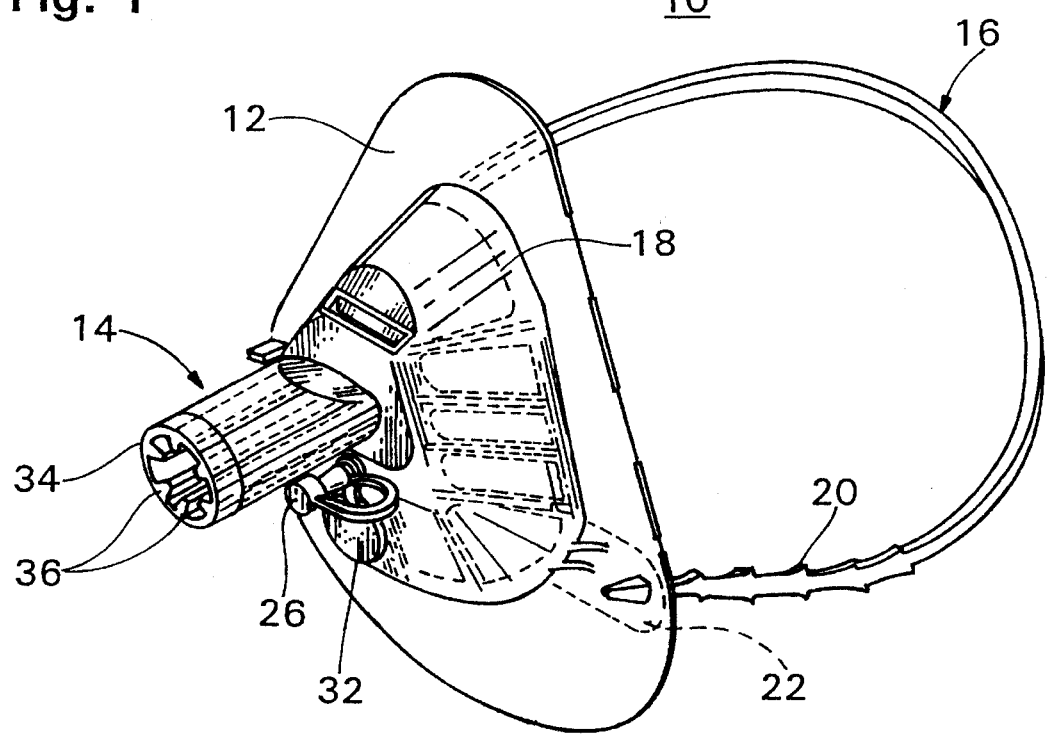
FIG. 1 is a perspective view of the cardiopulmonary resuscitation mask of the present invention.
Figure 2:
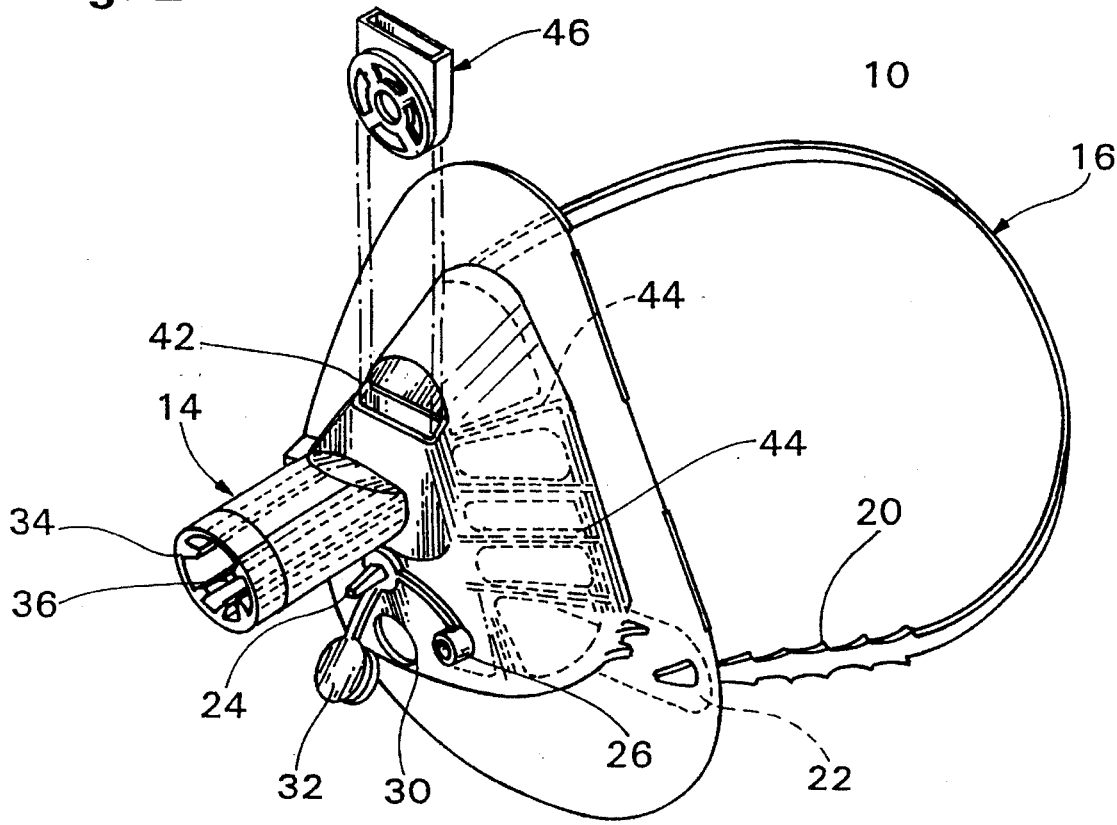
FIG. 2 is an exploded perspective view of the cardiopulmonary resuscitation mask of FIG. 1 including the duckbill valve assembly.
Figure 3:
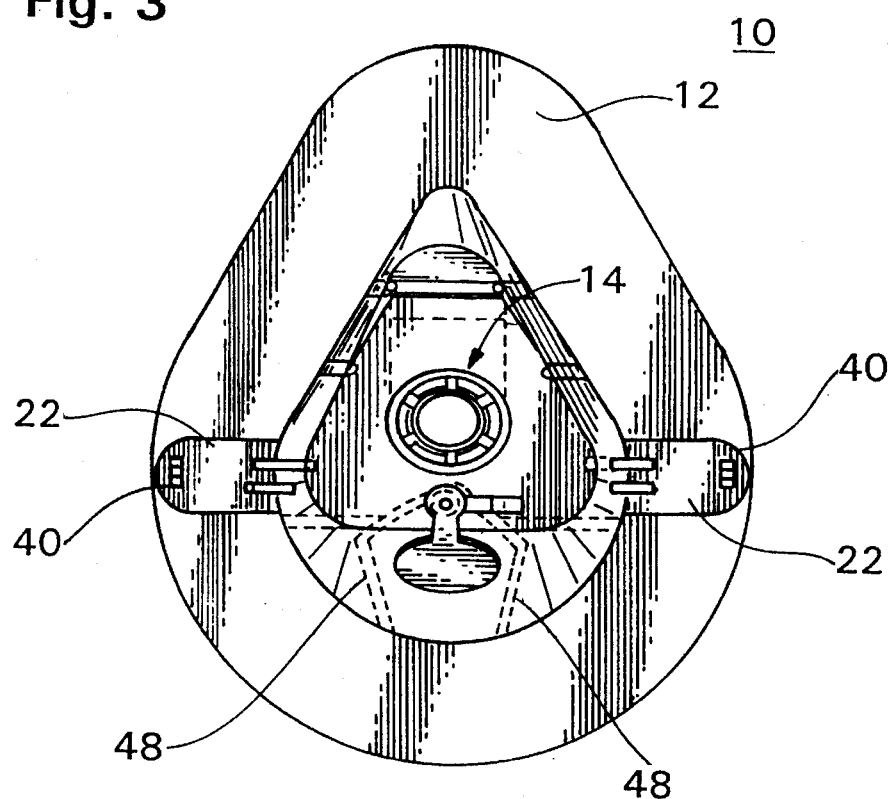
FIG. 3 is a front elevational view of the cardiopulmonary resuscitation mask of FIG. 1.
Figure 4:
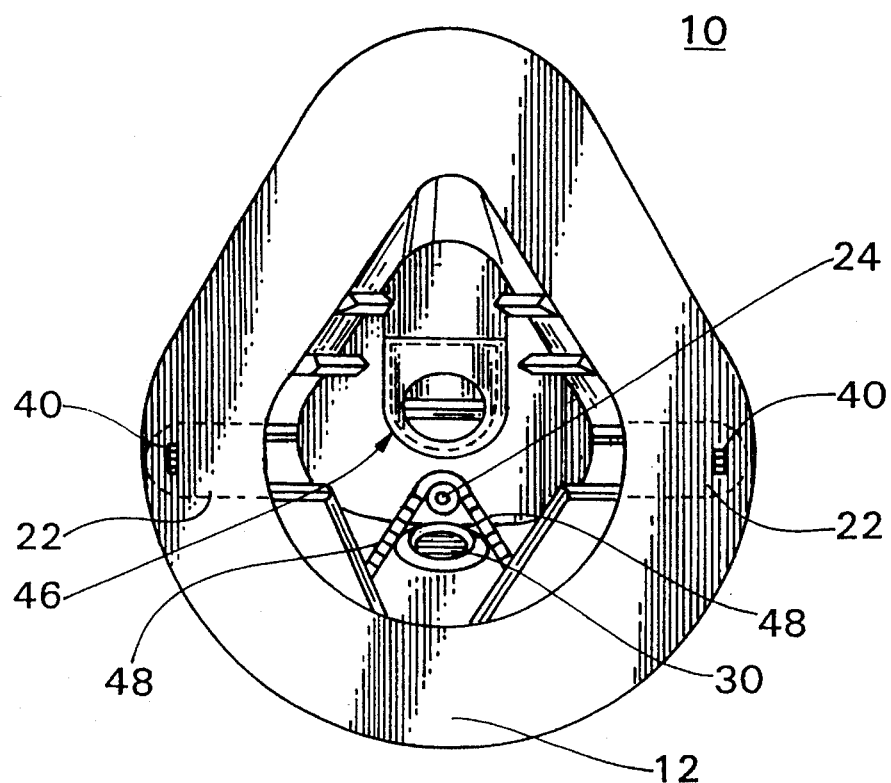
FIG. 4 is a rear elevational view of the cardiopulmonary resuscitation mask of FIG. 1.
Figure 5:
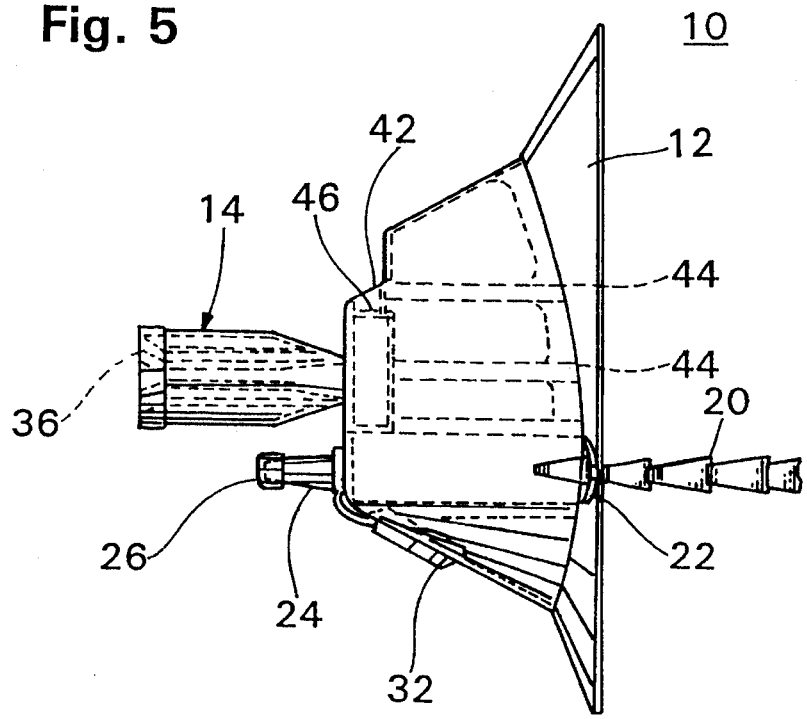
FIG. 5 is a side view of the cardiopulmonary resuscitation mask of FIG. 1.
Figure 6:
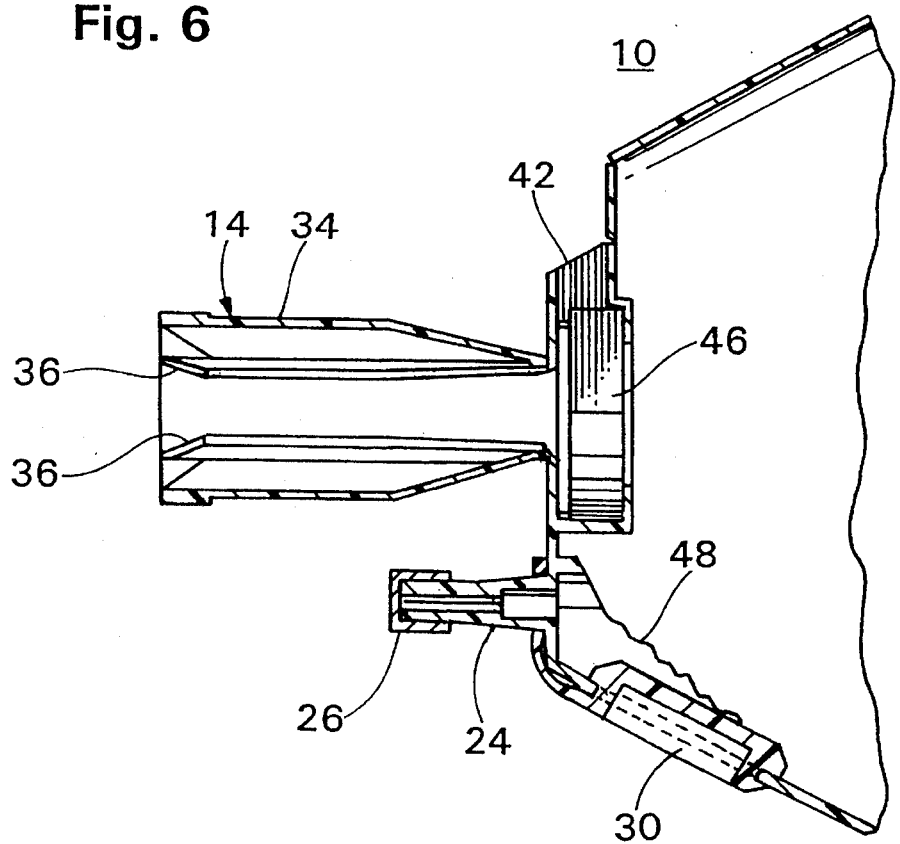
FIG. 6 is a fragmentary cross-sectional view of the cardiopulmonary resuscitation mask of FIG. 1.

Referring generally to FIGS. 1–6, there are shown various views of cardiopulmonary resuscitation mask 10 of the present invention. In these drawings, like numerals are used to indicate like elements throughout.

Cardiopulmonary resuscitation mask 10 of the present invention may be formed of generally transparent medical grade silicone and adapted to fit over the mouth and nose of a patient to provide a seal between sealing skirt 12 of mask 10 and the face of the patient. Resuscitation mask 10 includes mouthpiece 14 attached to generally cup-shaped region 18. Generally cup-shaped region 18 is surrounded by sealing skirt 12. Mouthpiece 14, cup-shaped region 18 and sealing skirt 12 are formed as a single unit in the preferred embodiment of resuscitation mask 10.

Resuscitation mask 10 is also provided with quickly tightenable head strap 16 for securing mask 10 to the head of the patient and causing sealing skirt 12 to be firmly pressed against the face of the patient. Head strap 16 of resuscitation mask 10 is provided with a series of gripping teeth 20 at each end. Gripping teeth 20 are adapted to pass easily through openings 40 in skirt reinforcing straps 22 of sealing skirt 12 when head strap 16 is tightened. Head strap 16 may be tightened as necessary in this manner to form the required seal between sealing skirt 12 and the face of the patient. Gripping teeth 20 then grip the edges of openings 40 to prevent head strap 16 from passing through openings 40 in the opposite direction and loosening. In this manner a sealed interior region is created between the face of the patient and generally cup-shaped region 18 of resuscitation mask 10.

Resuscitation mask 10 is provided with oxygen supply port 24. In the preferred embodiment of resuscitation mask 10 oxygen supply port 24 is provided with a thin tapered pipe of the luer type extending out of the front face of mask 10. This permits a standard oxygen supply coupling (not shown) to be easily applied to resuscitation mask 10 without removing resuscitation mask 10 from the face of the patient. It will be understood, however, that any type of port or detachable coupling may be used provided that it is effective to receive oxygen from an oxygen source and serve as a conduit for the received oxygen into the interior region formed by resuscitation mask 10. Cup-shaped region 18 in this manner serves as a container for containing the oxygen supplied to the patient. When oxygen support port 24 is not in use as a passageway it may be sealed using oxygen port cap 26.

Generally cup-shaped region 18 of resuscitation mask 10 is also provided with a second, larger, sealable port 30. Sealable port 30 is adapted to serve as a conduit to permit the patient to breathe more normally once resuscitation has been accomplished while continuing to permit a flow of oxygen to the patient as required by way of oxygen supply port 24. Additionally, sealable port 30 may be used for access to a patent in order to perform various patient monitoring procedures. Sealable port 30 may be sealed with port cap 32 when it is not in use.

Mouthpiece 14 includes generally cylindrical portion 34 which extends outwardly from the front of cup-shaped region 18 of resuscitation mask 10. Cylindrical portion 34 of mouthpiece 14 is adapted to be engaged by the mouth of the rescuer for forcing air into the lungs of the patient while performing cardiopulmonary resuscitation using resuscitation mask 10. Mouthpiece 14 also includes spacer ribs 36 disposed upon the inner surface of cylindrical portion 34. Spacer ribs 36 prevent cylindrical portion 34 from being totally closed if, for example, a rescuer bites down or otherwise squeezes cylindrical portion 34 of mouthpiece 14.

Mouthpiece 14 is formed as an elongated tube in the preferred embodiment of resuscitation mask 10. However, it will be understood by those skilled in the art that any type of opening or coupling device may be used provided it is effective to permit a rescuer to provide an air flow into the interior region contained by cup-shaped region 18. For example, mouthpiece 14 may be adapted to be coupled with a squeezable bag device for applying air to the interior region.

Figure 7:
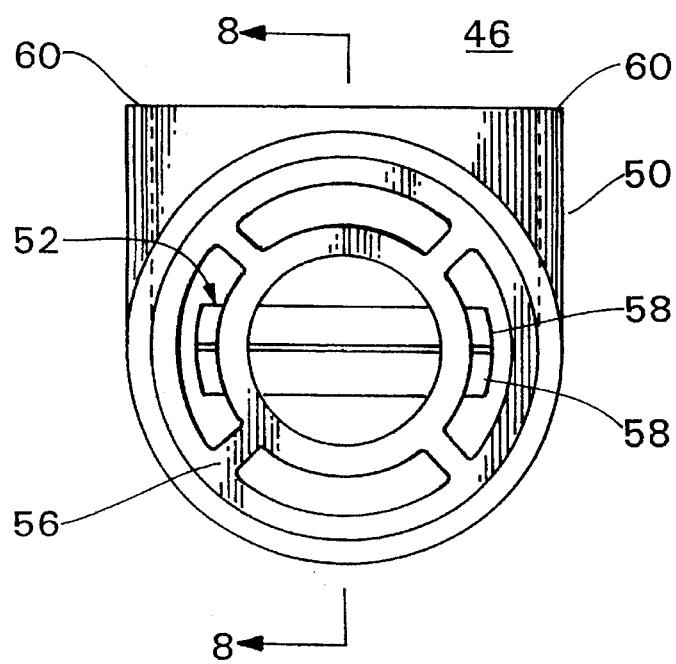
FIG. 7 is an enlarged view of the duckbill valve assembly of the cardiopulmonary resuscitation mask of FIG. 1.
Figure 8:
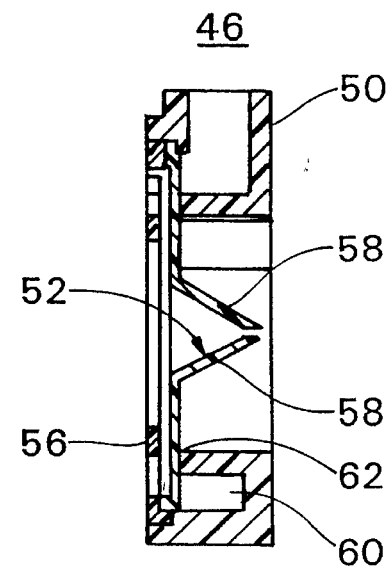
FIG. 8 is a cross-sectional view of the duckbill valve assembly of FIG. 7.
Figure 9:
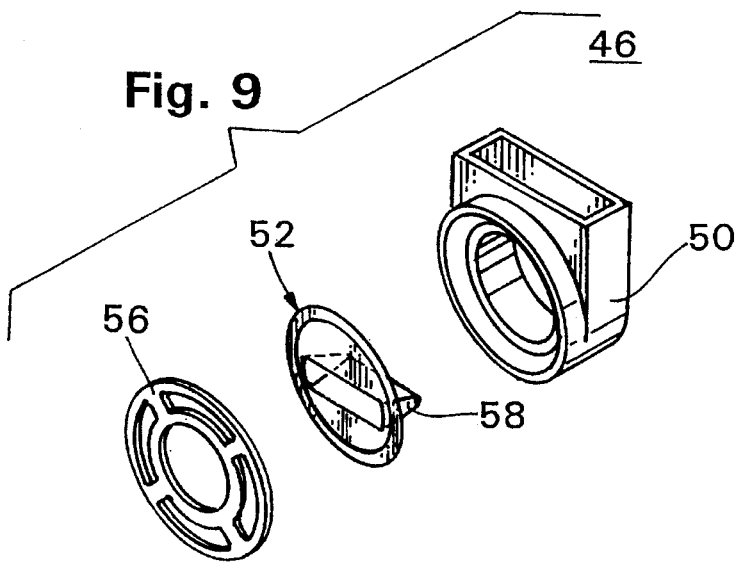
FIG. 9 is an exploded view of the duckbill valve assembly of FIG. 7.

Referring generally to FIGS. 7–9, there are shown various views of one-way valve assembly 46 of cardiopulmonary resuscitation mask 10. One-way valve assembly 46 may be a duckbill-type filter valve or any other type of valve adapted to permit air flow to pass in one direction while preventing air flow in the opposite direction. Slot 42 on the front face of resuscitation mask 10 above mouthpiece 14 receives valve assembly 46 in order to permit valve assembly 46 to be secured in resuscitation mask 10 at the rear of mouthpiece 14. Thus, air must pass through valve assembly 46 in order to pass through mouthpiece 14.

One-way valve assembly 46 includes valve housing 50 having a generally circular opening for receiving duckbill-type valve 52. Duckbill-type valve 52 is removably secured within valve housing 50 by rigid snap-in retainer 56. When a rescuer forces air into mouthpiece 14, two valve flaps 58 of duckbill-type valve 52 spread apart to allow air to enter the interior region of resuscitation mask 10. When the rescuer stops forcing air into mouthpiece 14 valve flaps 58 close against each other to provide a tight seal. This seal between flaps 58 prevents the passage of air, liquid, germs and other materials from the patient to the mouth of the rescuer by way of mouthpiece 14. 10 If the patient exhales, coughs or chokes or in any manner causes the air pressure within the interior region of resuscitation mask 10 to increase, flaps 58 of valve 52 thus stay closed and prevent air flow through mouthpiece 14. However, such an increase in air pressure within the interior region of resuscitation mask 10 causes valve 52 to bend slightly outwardly against rigid retainer 56 toward the mouth of the rescuer.

This outward motion of valve 52 is effective to provide fluid communication between the interior region of resuscitation mask 10 and annular passageway 60 within valve housing 50. By way of passageway 60 the interior region is thus placed in fluid communication with slot 42 and the exterior of resuscitation mask 10. This fluid communication may occur, for example, due to separation of valve 52 from housing 50 at abutment 62 as valve 52 is forced against rigid retainer 56 by increased pressure within the interior region of resuscitation mask 10. Pressure in the interior region of resuscitation mask 10 is thus released by way of slot 42 or conduit 42 in the front of resuscitation mask 10.

It will be understood that this release of pressure from within the interior region of resuscitation mask 10 may include the escape of air, liquids and other materials by way of slot 42. In this manner, pressure may be released from the interior region of resuscitation mask 10 without opening duckbill-type valve 52 and transporting materials to the mouth of the rescuer. Thus, valve 46 is adapted to both provide one-way air flow through mouthpiece 14 and to act as a pressure openable closure in order to provide venting by way of slot 42.

As previously described, resuscitation mask 10 of the present invention may be formed of a generally transparent medical grade silicon. However, it will be understood by those skilled in the art that resuscitation mask 10 may be formed of other materials which are suitable for containing the internal region. In the preferred embodiment of resuscitation mask 10 the materials should be flexible in order to permit easy folding. However, the material cannot be too flexible because resuscitation mask 10 must have sufficient structural integrity during use.

In order to provide additional structural integrity to cardiopulmonary resuscitation mask 10, the inner surface of cup-shaped region 18 is formed with a plurality of flexible strengthening ribs 44 or flexible reinforcing ribs 44. Flexible reinforcing ribs 44 permit plastic resuscitation mask 10 to be folded and conveniently packaged in a small container (not shown) while providing mask 10 with sufficient structural integrity when installed on the face of a patient. Thus, resuscitation mask 10 may be stored in a very small amount of space along with other rescue equipment and, when unfolded, it can withstand the stresses applied to it by the rescuer and the oxygen source.

Generally V-shaped reinforcing ribs 48 surrounding oxygen supply port 24 may also be provided within cup-shaped region 18 of resuscitation mask 10 in order to provide extra support to this region when an oxygen source is coupled to oxygen supply port 24. In addition to reinforcing the region around oxygen supply port 24 reinforcing ribs 48 serves as an air flow barrier. This air flow barrier helps prevent a venturi effect and entrainment within resuscitation mask 10 as a result of the pressure supplied by an oxygen source. Cardiopulmonary resuscitation mask 10 is also adapted to be disposable. Thus, after a single use resuscitation mask 10 may be discarded.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A resuscitation mask comprising:
   a mask wall defining an interior region between the mask wall and a patient's face;
   a mouthpiece conduit extending out from said mask wall and defining a first flow passage from outside the mask wall to the interior region, said mouthpiece conduit having spacer ribs disposed therein, said spacer ribs preventing collapse of said mouthpiece conduit;
   a one-way valve removably inserted into said mouthpiece conduit, said one-way valve restricting air flow through said mouthpiece conduit from said interior region to outside the mask;
   an oxygen port having a removable cap, said oxygen port extending out from said mask wall and defining a second flow passage from outside said mask wall and the interior region;
   means for acting as an air flow barrier and for preventing air from being drawn into said mask by a venturi effect caused by a high flow of oxygen through the oxygen port, said air flow barrier means comprising reinforcing ribs surrounding said oxygen port; and
   a patient breathing port having a removable cap, said patient breathing port with its associated cap removed adapted to permit a patient to breathe ambient air.

2. The resuscitation mask of claim 1, wherein said mouthpiece conduit comprises a flexible, cylindrical member.

3. The resuscitation mask of claim 1, wherein said oxygen port comprises a detachable coupling for detachably applying an oxygen source to said oxygen port.

4. The resuscitation mask of claim 1, wherein said reinforcing ribs are flexible permitting folding of said mask and providing reinforcement of said mask when said mask is unfolded.

5. The resuscitation mask of claim 1, wherein said mask wall further comprises a surrounding skirt for sealing said mask wall with a patient's face.

6. A resuscitation mask comprising:
   a mask wall defining an interior region between the mask wall and a patient's face;
   a mouthpiece conduit extending out from said mask wall and defining a first flow passage from outside the mask wall to the interior region, said mouthpiece conduit having spacer ribs disposed therein, said spacer ribs preventing collapse of said mouthpiece conduit;
   a one-way valve removably inserted into said mouthpiece conduit, said one-way valve restricting air flow through said mouthpiece conduit from said interior region to outside the mask;
   an oxygen port having a removable cap, said oxygen port extending out from said mask wall and defining a second flow passage from outside said mask wall and the interior region;
   means for acting as an air flow barrier and for preventing air from being drawn into said mask by a venturi effect caused by a high flow of oxygen through the oxygen port, said air flow barrier means comprising reinforcing ribs surrounding said oxygen port.

7. The resuscitation mask of claim 6 wherein, said oxygen port is provided with a detachable coupling for detachably applying an oxygen source to said oxygen port.

8. The resuscitation mask of claim 6, wherein said first flow passage comprises a cylindrical member.

9. The resuscitation mask of claim 6, wherein said reinforcing ribs are flexible permitting folding of said mask and providing reinforcement of said mask when said mask is unfolded.

10. The resuscitation mask of claim 6, wherein said mask wall further comprises a surrounding skirt for sealing said mask wall to a patient's face.

* * * * *